(12) United States Patent
Evers et al.

(10) Patent No.: US 8,030,320 B2
(45) Date of Patent: Oct. 4, 2011

(54) DERIVATIVES OF 1-OXO-1,2-DIHYDROISOQUINOLINE-5-CARBOXAMIDES AND OF 4-OXO-3,4-DIHYDROQUINAZOLINE-8-CARBOXAMIDES, PREPARATION THEREOF AND APPLICATION THEREOF IN THERAPEUTICS

(75) Inventors: Michel Evers, La Queue En Brie (FR); Arielle Genevois-Borella, Thiais (FR); Andreas Karlsson, Paris (FR); Jean-Luc Malleron, Marcoussis (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 12/693,598

(22) Filed: Jan. 26, 2010

(65) Prior Publication Data

US 2010/0197706 A1     Aug. 5, 2010

Related U.S. Application Data

(63) Continuation of application No. PCT/FR2008/001109, filed on Jul. 25, 2008.

(30) Foreign Application Priority Data

Jul. 27, 2007 (FR) ...................................... 07 05500

(51) Int. Cl.
*A61K 31/517* (2006.01)
(52) U.S. Cl. ...................................... 514/266.3; 544/287
(58) Field of Classification Search .................... 544/287
See application file for complete search history.

(56) References Cited

U.S. PATENT DOCUMENTS 7,176,242 B2 *   2/2007   John et al. ...................... 514/615

FOREIGN PATENT DOCUMENTS

| EP | 1477490 | 11/2004 |
|---|---|---|
| WO | WO 03/040096 | 5/2003 |
| WO | WO 2004/094430 | 11/2004 |
| WO | WO 2005/058915 | 6/2005 |
| WO | WO 2006/099352 | 9/2006 |
| WO | WO 2006/103088 | 10/2006 |

OTHER PUBLICATIONS

Beher, D., et al., Protease Inhibitors as Potential Disease-Modifying Therapeutics for Alzheimer's Disease, Expert Opin. Invest. Drugs, vol. 14, pp. 1385-1409, (2005).
Citron, M., et. al., Strategies for Diease Modification in Alzheimer's Disease, Nature Reviews, vol. 5, (2004), pp. 677-685.
Durham, T. B., et. al., Progress Towards the Discovery and Development of Efficacious BACE inhibitors, Curr. Opin. Drug Disc. Dev., vol. 9, pp. 776-791, (2006).
Ghosh, A. K., et. al., B-Secretase as a Therapeutic Target for Inhibitor Drugs, Current Medicinal Chemistry. vol. 9, pp. 1135-1144, (2002).
Kisfaludy, L., et. al., Rapid and Selective Formylation With Pentafluorophenyl Formate, Synthesis, vol. 5, pp. 510, (1987).
Wiedemann, S., et. al., Primary 1-Arylcyclopropylamines from Aryl Cyanides With Diethylzinc and Titanium Alkoxides, Organic Letters, vol. 5, No. 5, pp. 753-755, (2003).
Ben-David, Y., et. al., Chelate-Assisted, Pd-Catalyzed Efficient Carbonylation of Aryl Chlorides, J. Am. Chem. Soc., (1989), vol. 111, pp. 8742-8744.
Ermolieff, J., et. al., Proteolytic Activation of Recombinant Pro-Memapsin 2 (Pro-B-Secretase) Studied With New Fluorogenic Substrates, Biochemistry, vol. 39, pp. 12450-12456, (2000).
Ku, T. W., et. al., An Alternate Enantiospecific Synthesis of Methyl (S)-7-Tert-Butoxycarbonyl-2,3,4,5-Tetrahydro-4-Methyl-3-Oxo-1H-1,4-Benzodiazepine-2-Acetate, Tetrahedron Letters, vol. 38, No. 18, pp. 3131-3134, (1997).
Orito, K., et. al., Preparation of Benzolactams by Pd(OAc)2-Catalyzed Direct Aromatic Carbonylation, J. Am. Chem. Soc., (2004), vol. 126, pp. 14342-14343.
Wang, Y-C., et. al., An Efficient Synthesis of Thalifoline, Synthesis, (2002), vol. 15, pp. 2187-2190.
Ferrer, S., et. al., N- and O-Alkylation of Isoquinolin-1-ones in The Mitsunobu Reaction: Development of Potential Drug Delivery Systems, J. Chem. Soc., Perkin Trans. 1, (2002), pp. 335-340.
Selkoe, D. J., et. al., Translating Cell Biology Into Therapeutic Advance's in Alzheimer's Disease, Nature, vol. 399, (1999), pp. A23-A31.
Roggo, S., et. al., Inhibition of BACE, A Promising Approach to Alzheimer's Disease Therapy, Current Topics in Medicinal Chemistry, (2002), vol. 2, pp. 359-370.

* cited by examiner

*Primary Examiner* — James O Wilson
*Assistant Examiner* — Brian McDowell
(74) *Attorney, Agent, or Firm* — Scully, Scott, Murphy & Presser, P.C.

(57) ABSTRACT

The present invention relates to compounds of formula I, (I)

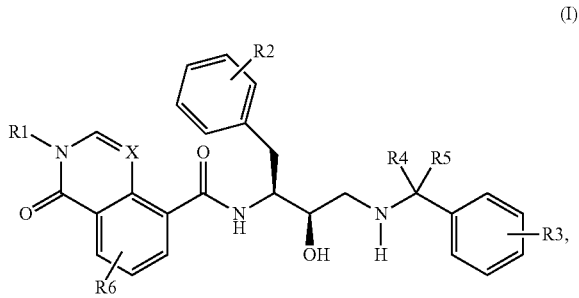

to the preparation thereof and to the therapeutic use thereof.

6 Claims, No Drawings

DERIVATIVES OF 1-OXO-1,2-DIHYDROISOQUINOLINE-5-CARBOXAMIDES AND OF 4-OXO-3,4-DIHYDROQUINAZOLINE-8-CARBOXAMIDES, PREPARATION THEREOF AND APPLICATION THEREOF IN THERAPEUTICS

This is a Continuation of International Application No. PCT/FR2008/001109, filed Jul. 25, 2008, which is incorporated herein by reference in its entirety.

The present invention relates to derivatives of 1-oxo-1,2-dihydroisoquinoline-5-carboxamides and of 1-oxo-3,4-dihydroquinazoline-8-carboxamides, to the preparation thereof and to the therapeutic use thereof.

The presence of multiple senile plaques in brain tissue is one of the main histopathological alterations observed in Alzheimer's disease, these plaques form by deposition of fibrillary aggregates of a 4 kDa peptide (40-42 amino acids), known as amyloid β (Aβ) peptide. The production and gradual accumulation of this peptide could play a crucial role in the triggering and progression of Alzheimer's pathology, according to the amyloid cascade hypothesis (D. Seiko et al. Nature 399A (1999) 23; S. Roggo et al. Top. Med. Chem. 2 (2002) 359; A. Ghosh et al. Curr. Med. Chem. 9 (2002) 1135).

The Aβ peptide originates from the APP (Amyloid Precursor Protein) protein, which may be cleaved by at least three different proteolytic activities: 1) cleavage in the Aβ region by an a-secretase activity (thus preventing the formation of Aβ); 2) cleavage at the N-terminal end of Aβ by a β-secretase activity; 3) cleavage at the C-terminal end of Aβ by a γ-secretase activity. The consecutive cleavage of the APP protein at the β and γ sites leads to the formation of the Aβ peptide (M. Citron Nat. Rev. Neurosci. 5 (2004) 677-685; D. Beher et al. Expert Opin. Invest. Drugs 14 (2005) 1385-1409).

There is therefore a real interest in finding compounds that inhibit the production of the Aβ peptide (T. B. Durham et al. Curr. Opin. Drug Disc. Dev. 9 (2006) 776-791).

It has now been found that compounds, derivatives of 1-oxo-1,2-dihydroisoquinoline-5-carboxamides and of 1-oxo-3,4-dihydroquinazoline-8-carboxamides, possess a strong inhibitory activity with respect to the β-secretase activity.

One subject of the present invention is the compounds corresponding to the formula (I):

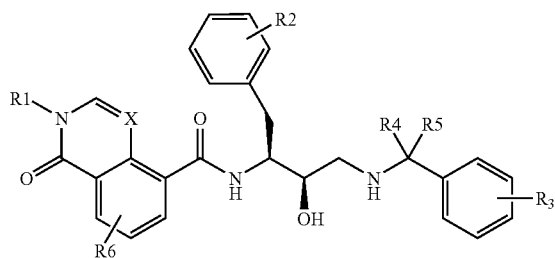

(I)

in which:
R1 represents a hydrogen atom, a $(C_1-C_{10})$alkyl, $(C_3-C_7)$cycloalkyl, $(CH_2)_n-(C_1-C_6)$alkenyl, $(CH_2)_n-(C_1-C_6)$alkynyl or $(C_1-C_6)$alkyl-Z—$(C_1-C_6)$alkyl group, in which Z represents a heteroatom chosen from O, N and $S(O)_m$, or else R1 represents a COOR, $S(O)_mR$, aryl or aralkyl group; the $(C_1-C_{10})$alkyl, $(C_3-C_7)$cycloalkyl, $(CH_2)_n-(C_1-C_6)$alkenyl, $(CH_2)_n-(C_1-C_6)$alkynyl, $(C_1-C_6)$alkyl-Z—$(C_1-C_6)$alkyl, aryl or aralkyl groups being optionally substituted with one or more groups chosen from a halogen atom, a $(C_1-C_6)$alkyl, $(C_3-C_7)$cycloalkyl, halo$(C_1-C_6)$alkyl, $(C_1-C_6)$alkoxy, halo$(C_1-C_6)$alkoxy, NR7R8, nitro, cyano, OR, COOR, CONR7R8 or $S(O)_m$NR7R8 group or an aryl group;

R2 represents one or more groups chosen from a hydrogen atom, a halogen atom, a $(C_1-C_6)$alkyl, $(C_3-C_7)$cycloalkyl, $(C_1-C_6)$alkenyl, $(C_1-C_6)$alkynyl or $(C_1-C_6)$alkyl-Z—$(C_1-C_6)$ alkyl group, in which Z represents a heteroatom chosen from O, N and $S(O)_m$, or else $R^2$ represents a halo$(C_1-C_6)$alkyl, halo$(C_1-C_6)$alkoxy, hydroxy, $(C_1-C_6)$alkoxy, nitro, cyano or amino group, an NR7R8, COOR, CONR7R8, OCO$(C_1-C_6)$ alkyl or $S(O)_m$—NR7R8 group, or an aryl group, said aryl group possibly being optionally substituted with one or more groups chosen from a halogen atom, a $(C_1-C_6)$alkyl, $(C_3-C_7)$cycloalkyl, halo$(C_1-C_6)$alkyl, $(C_1-C_6)$alkoxy, halo$(C_1-C_6)$alkoxy, NR7R8, OR, nitro, cyano, COOR, CONR7R8 or $S(O)_m$NR7R8 group;

R3 represents a trifluoromethyl group;

R4 and R5 represent a hydrogen atom, or else R4 and R5 form, with the carbon atom that bears them, a saturated ring containing from 3 to 6 carbon atoms and optionally containing from 0 to 1 heteroatom, chosen from O, N or S;

R6 represents a group chosen from a hydrogen atom, a halogen atom, a $(C_1-C_6)$alkyl, $(C_3-C_7)$cycloalkyl or $(C_3-C_7)$cycloalkyl$(C_1-C_6)$alkyl group, a halo$(C_1-C_6)$alkyl, nitro or amino group, an NR7R8 or COOR group, an NR7(SO$_2$)R8 or CONR7R8 group or an aryl group, said aryl group being optionally substituted with one or more groups chosen from a halogen atom, a $(C_1-C_6)$alkyl, $(C_1-C_6)$alkoxy or cyano group;

R, R7 and R8 represent, independently of one another, one or more groups chosen from a hydrogen atom, a $(C_1-C_6)$alkyl, $(C_3-C_7)$cycloalkyl or $(C_3-C_7)$cycloalkyl$(C_1-C_6)$alkyl group, an aryl or aryl$(C_1-C_6)$alkylene group, or else R7 and R8 may form, with the atom which bears them, a saturated, partially unsaturated or unsaturated ring containing from 5 to 7 carbon atoms and optionally containing, in addition, a heteroatom chosen from O, N or $S(O)_m$;

X represents a carbon atom or a nitrogen atom;

m represents an integer which may take the values 0, 1 or 2 and n represents an integer which may take the values 1, 2, 3, 4, 5 or 6;

the carbon bearing the benzyl group substituted by R2 is of S absolute configuration; and the carbon bearing the hydroxyl group is of R absolute configuration.

The compounds of formula (I) may comprise one or more asymmetric carbon atoms. They may therefore exist in the form of enantiomers or of diastereoisomers. These enantiomers or diastereoisomers, and also mixtures thereof, including racemic mixtures, are part of the invention.

The compounds of formula (I) may exist in the form of bases or addition salts with acids. Such addition salts are part of the invention.

These salts may be prepared with pharmaceutically acceptable acids, but the salts of other acids that are useful, for example, for the purification or isolation of the compounds of formula (I) are also part of the invention.

Within the context of the present invention, the following definitions apply:

$C_t$-$C_z$, where t and z may take the values of 1 to 10, is understood to mean a carbon-based chain or ring which may have from t to z carbon atoms, for example $C_1$-$C_3$ may characterize a carbon-based chain having from 1 to 3 carbon atoms;

a halogen atom: a fluorine, a chlorine, a bromine or an iodine;

an alkyl group: a linear or branched saturated aliphatic group. By way of examples, mention may be made of the methyl, ethyl, propyl, isopropyl, butyl, isobutyl, tert-butyl, pentyl, etc. groups;

a cycloalkyl group: a cyclic alkyl group. By way of examples, mention may be made of the cyclopropyl, methylcyclopropyl, cyclobutyl, cyclopentyl, cyclohexyl, etc. groups;

an alkylene group: a linear or branched saturated divalent aliphatic group. By way of example, a $C_{1-3}$-alkylene group represents a linear or branched divalent carbon-based chain having 1 to 3 carbon atoms, such as a methylenyl (—$CH_2$—), an ethylenyl (—$CH_2CH_2$—), a 1-methylethylenyl (—$CH(CH_3)CH_2$—) or a propylenyl (—$CH_2CH_2CH_2$—);

an alkenyl group: a linear or branched monounsaturated or polyunsaturated aliphatic group comprising, for example, one or two ethylenically unsaturated groups;

an alkynyl group: a linear or branched monounsaturated or polyunsaturated aliphatic group comprising, for example, one or two acetylenically unsaturated groups;

an alkoxy group: an —O-alkyl radical where the alkyl group is as defined previously;

a halo($C_1$-$C_6$)alkyl group: an alkyl group of which one or more hydrogen atoms have been substituted with a halogen atom. By way of examples, mention may be made of the $CF_3$, $CH_2CF_3$, $CHF_2$ or $CCl_3$ groups;

a halo($C_1$-$C_6$)alkoxy group: an —O-alkyl radical where the alkyl group is as defined previously and which is substituted by one or more identical or different halogen atoms. By way of examples, mention may be made of the $OCF_3$, $OCHF_2$ or $OCCl_3$ groups;

the sulfur and nitrogen atoms may be present in the oxidized state (N-oxide, sulfoxide, sulfone, etc.);

an aryl group: a cyclic aromatic group comprising between 6 and 14 carbon atoms. By way of example of an aryl group, mention may be made of phenyl or naphthyl.

Among the compounds of formula (I) that are subjects of the invention, a first group of compounds is constituted by the compounds for which:

X represents a carbon atom.

Among the compounds of formula (I) that are subjects of the invention, a second group of compounds is constituted by the compounds for which:

X represents a nitrogen atom.

Among the compounds of formula (I) that are subjects of the invention, a third group of compounds is constituted by the compounds for which:

R1 represents a ($C_1$-$C_{10}$)alkyl group, optionally substituted with one or more ($C_1$-$C_6$)alkyl groups;

R2, R4 and R5 represent a hydrogen atom; and

R6 represents a group chosen from a hydrogen atom or a halogen atom.

The combinations of groups one to three as defined above are also part of the invention.

Among the compounds of formula (I) that are subjects of the invention, mention may especially be made of the following compounds:

N-[(1S,2R)-1-benzyl-2-hydroxy-3-{[3-(trifluoromethyl)benzyl]amino}-propyl]-1-oxo-2-(1-propylbutyl)-1,2-dihydroisoquinoline-5-carboxamide and its hydrochloride (1:1)

N-[(1S,2R)-1-benzyl-2-hydroxy-3-{[3-(trifluoromethyl)benzyl]amino}-propyl]-6-chloro-4-oxo-3-(1-propylbutyl)-3,4-dihydroquinazoline-8-carboxamide and its hydrochloride (1:1)

N-[(1S,2R)-1-benzyl-2-hydroxy-3-{[3-(trifluoromethyl)benzyl]amino}-propyl]-4-oxo-3-(1-propylbutyl)-3,4-dihydroquinazoline-8-carboxamide and its hydrochloride (1:1).

Another subject of the invention is a method for preparing the compounds of formula (I).

In what follows, the expression "protective group Pg" is understood to mean a group which makes it possible, on the one hand, to protect a reactive functional group such as a hydroxyl or an amine during a synthesis and, on the other hand, to regenerate the reactive functional group intact at the end of the synthesis. Examples of protective groups and also of methods of protection and of deprotection are given in "Protective Groups in Organic Synthesis", Green et al., $2^{nd}$ Edition (John Wiley & Sons, Inc., New York), 1991.

The expression "leaving group" is understood to mean, in what follows, a group which may be easily cleaved from a molecule by rupture of a heterolytic bond, with departure of an electron pair. This group may thus be easily replaced by another group during a substitution reaction for example. Such leaving groups are, for example, halogens or an activated hydroxyl group such as a methanesulfonate, benzenesulfonate, p-toluenesulfonate, triflate, acetate, etc. Examples of leaving groups and also references for the preparation thereof are given in "Advances in Organic Chemistry", J. March, $3^{rd}$ Edition, Wiley Interscience, 1985, p. 310-316.

In the schemes which follow, the starting compounds and the reactants, when their method of preparation is not described, are commercially available or are described in the literature, or else may be prepared according to methods which are described therein or which are known to a person skilled in the art.

The abbreviations and symbols used for the description of the methods of synthesis and for the description of the compounds are the following:

BOC for tert-butoxycarboxylate,
DCC for dicyclohexylcarbodiimide,
DMF for dimethylformamide,
EDCI for (1-ethyl-3,3-dimethylaminopropyl)carbodiimide,
NMP for N-methyl-2-pyrrolidone,
PyBOP for benzotriazol-1-yloxytripyrrolidinophosphonium hexafluorophosphate,
THF for tetrahydrofuran.

In accordance with the invention, it is possible to prepare the compounds of general formula (I) according to the method illustrated by scheme 1 below.

Scheme 1

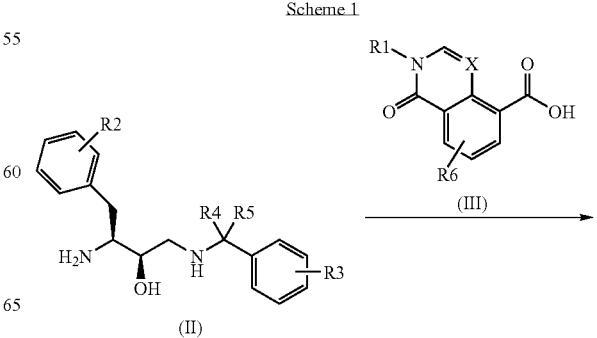

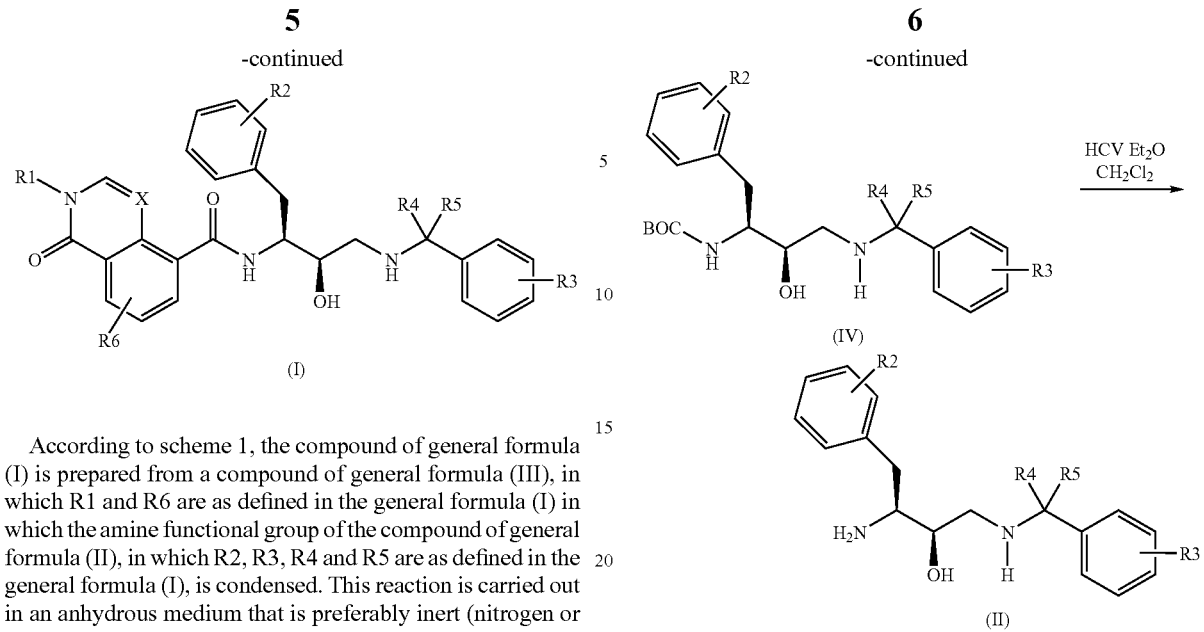

According to scheme 1, the compound of general formula (I) is prepared from a compound of general formula (III), in which R1 and R6 are as defined in the general formula (I) in which the amine functional group of the compound of general formula (II), in which R2, R3, R4 and R5 are as defined in the general formula (I), is condensed. This reaction is carried out in an anhydrous medium that is preferably inert (nitrogen or argon for example) and by using conventional agents for coupling an acid with an amine such as DCC, PyBOP or EDCI, in solvents such as dichloromethane, THF, ether or chloroform at a temperature between 20° C. and the reflux temperature of the solvent.

The compound of general formula (II), in which R2, R3, R4 and R5 are as defined in the general formula (I), may be prepared from the compound of general formula (IV), in which R2, R3, R4 and R5 are as defined in the general formula (I), by deprotection of the primary amine by action of an acid (for example hydrochloric acid) in solution in a solvent or a solvent mixture that is etherated (for example diethyl ether) and/or chlorinated (for example dichloromethane), according to the method illustrated by scheme 2 below.

The compound of general formula (IV), in which R2, R3, R4 and R5 are as defined in the general formula (I), may be prepared by reacting a benzylamine derivative of general formula (VI), for which R3, R4 and R5 are as defined in the general formula (I) with an oxirane of general formula (V), for which R2 is as defined in the general formula (I) by operating in an anhydrous medium that is preferably inert (nitrogen or argon for example), in a chlorinated solvent (for example dichloromethane) and in the presence of a triflate anion (for example, scandium triflate).

Scheme 2

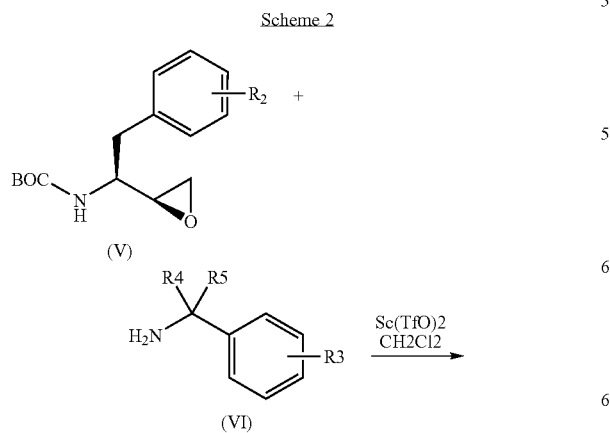

The compounds of general formula (IIIa) in which X represents a carbon atom and R1 is as described previously may be prepared according to the method described in scheme 3 below.

Scheme 3

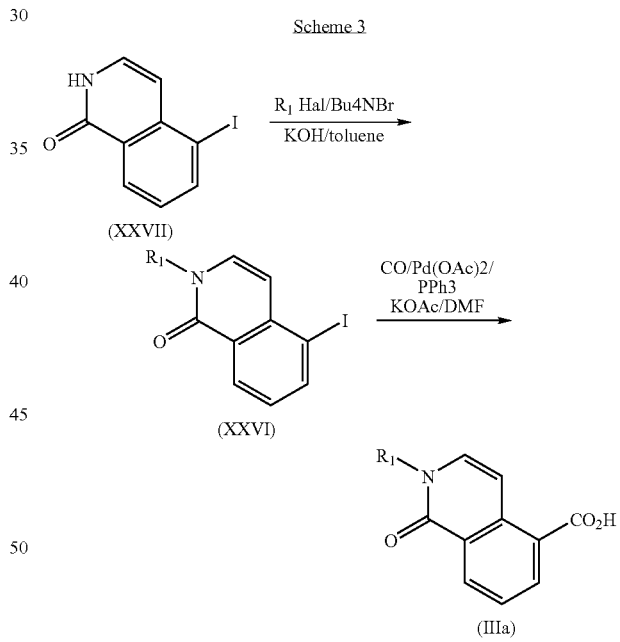

The compounds of general formula (IIIa) may be obtained from compounds of general formula (XXVI) reacted with carbon monoxide in the presence of (potassium or sodium) acetate ions, an alkali metal iodide (sodium iodide or potassium iodide for example), a palladium catalyst (palladium acetate for example), a phosphine (triphenylphosphine for example) in solution in an organic solvent (dimethylformamide or dimethylsulfoxide for example) and in the presence of water. The reaction takes place under a carbon monoxide pressure of 1 to 100 atmospheres and at a temperature between 20° C. and 120° C., by analogy with the works of D. Milstein et al. J. Am. Chem. Soc. (1989) 8742 and T. W. Ku et al. Tetrahedron Lett. (1997) 3131.

The compounds of general formula (XXVI) may be prepared from 5-iodo-2H-isoquinolin-1-one, described in the literature (M. D. Threadgill et al., J. Chem. Soc. Perkin Trans. 1 (2002) 335), after alkylation with an alkylating agent of general formula R1-Hal. The reaction takes place in solution in an organic solvent (for example toluene or dichloromethane) in the presence of a base (for example sodium hydroxide, potassium hydroxide or sodium hydride) and a tetraalkylammonium halide (for example tetrabutylammonium bromide) and at a temperature between 20° C. and the reflux temperature of the solvent.

The compounds of general formula (IIIb), for which X represents a nitrogen atom, R6 represents a halogen atom for example chlorine, and R1 is as described previously, may be prepared according to the method described in scheme 4 below.

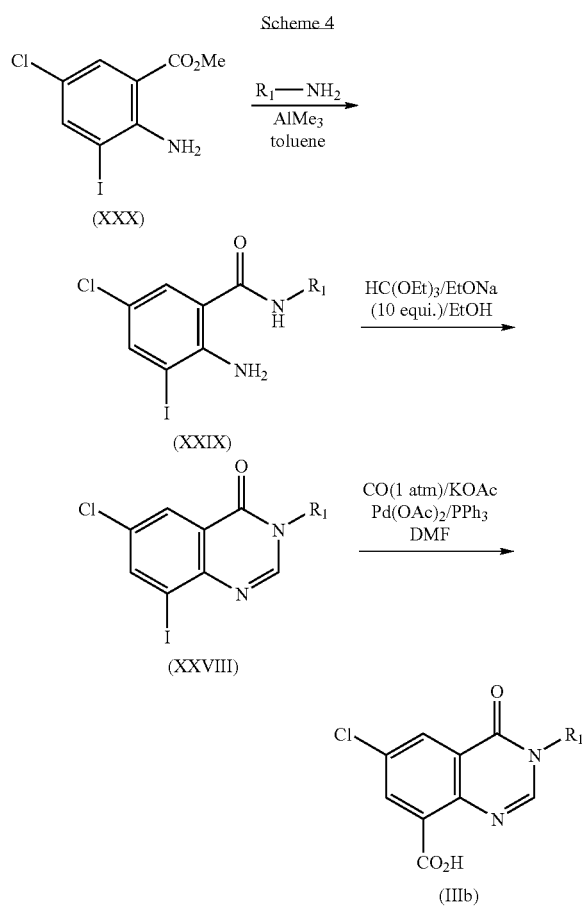

The compounds of general formula (IIIb) may be obtained from compounds of general formula (XXVIII) under the same conditions as those used for the preparation of compounds of general formula (IIIa).

The compounds of general formula (XXVIII) may be prepared by action of an orthoformate (methyl orthoformate for example) in the presence of a base (sodium methanolate or sodium ethanolate for example) on compounds of general formula (XXIX) in solution in an alcoholic solvent (methanol or ethanol for example). The reaction preferably takes place at a temperature between 0° C. and the reflux temperature of the solvent.

The compounds of general formula (XXIX) may be prepared by action of an amine of general formula R1—NH$_2$ on methyl 2-amino-5-chloro-3-iodobenzoate in the presence of a trimethylaluminum in an organic solvent (toluene for example) at a temperature between 20° C. and the reflux temperature of the solvent.

The compounds of formula (IIIa) and (IIIb) are useful as synthesis intermediates of the compounds of formula (I).

The products of formula (I) may be subjected, if desired and if necessary, in order to obtain products of formula (I) or to be converted into other products of formula (I), to one or more of the following conversion reactions, in any order:

a) an esterification or amidification reaction of an acid functional group;
b) a hydrolysis reaction of an ester functional group to an acid functional group;
c) a reaction for conversion of a hydroxyl functional group to an alkoxy functional group;
d) an oxidation reaction of an alcohol functional group to an aldehyde, ketone or acid functional group;
e) a reduction reaction of an acid, aldehyde or ketone functional group to an alcohol functional group;
f) a reductive amination reaction of an aldehyde or ketone functional group;
g) an oxidation reaction of an alkenyl group to an aldehyde or ketone functional group;
h) an oxidation reaction of a thioether to a sulfone or sulfoxide;
i) an alkylation reaction of a sulfonamide;
j) a dehydration reaction of a hydroxyalkyl group to an alkenyl group;
k) a dehydrohalogenation reaction of a halogenated derivative;
l) a total or partial hydrogenation reaction of an alkenyl or alkynyl group to an alkenyl or alkyl group;
m) a catalytic coupling reaction of a halogenated derivative and of an organometallic derivative such as a stannic or boronic derivative in order to introduce an alkyl, alkenyl, alkynyl or aryl substituent;
n) a reaction for protecting reactive functional groups;
o) a reaction for eliminating protective groups that the protected reactive functional groups may bear;
p) a salification reaction by a mineral or organic acid or by a base in order to obtain the corresponding salt;
q) a reaction for resolution of racemic forms into enantiomers, said products of formula (I) thus obtained being, where appropriate, in all the possible racemic, enantiomeric and diastereoisomeric isomer forms;
r) a reduction reaction of nitro derivatives to nitroso or amino derivatives;
s) a monoalkylation or dialkylation reaction of an amine functional group;
t) a sulfonylation reaction of a primary or secondary amine; and
u) an acylation reaction of an amine functional group.

The compounds of formula (I) may be purified by methods known to a person skilled in the art, for example by crystallization, chromatography or extraction.

In schemes 1 to 4 the starting compounds and the reactants, when their method of preparation is not described, are commercially available or are described in the literature, or else may be prepared according to methods which are described therein or which are known to a person skilled in the art.

The following examples describe the preparation of certain compounds in accordance with the invention. These examples are not limiting and serve only to illustrate the present invention. The numbers of the compounds exemplified refer to those given in the table below, which illustrates the chemical structures and the physical properties of a few compounds according to the invention.

The nomenclature of the exemplified compounds below was established using ACDLabs® Version 10.0 software.

The proton nuclear magnetic resonance ($^1$H NMR) spectra were performed at 250 MHz, 300 MHz, 400 MHz or 500 MHz on Brüker machines (chemical shifts (δ in ppm)—in the solvent dimethylsulfoxide—$d_6$ (DMSO-$d_6$) referenced to 2.50 ppm at the temperature of 303K). The abbreviations used for characterizing the signals are the following: s=singlet, m=multiplet, d=doublet, t=triplet, q=quadruplet.

EXAMPLE 1

The preparation of 5-iodo-2H-isoquinolin-1-one is described in the literature: Threadgill, M. D. et coll., J. Chem. Soc., Perkin Trans. 1, 2002, 335.

1.1: Base N-[(1S,2R)-1-benzyl-2-hydroxy-3-{[3-(trifluoromethyl)benzyl]-amino}propyl]-1-oxo-2-(1-propylbutyl)-1,2-dihydroisoquinoline-5-carboxamide 1.1.1: 5-iodo-2-(1-propylbutyl)isoquinolin-1(2H)-one 0.2 g of 5-iodo-2H-isoquinolin-1-one, 234 mg of 4-bromoheptane, 62 mg of finely ground potassium hydroxide, 79 mg of tetrabutylammonium bromide then 28 cm$^3$ of toluene are stirred, under an inert atmosphere, for 6 h at the reflux of the solvent. The reaction mixture is filtered through sintered glass. The filtrate is concentrated using a rotary evaporator under reduced pressure (5 kPa). The 320 mg of brown oil obtained are purified by flash chromatography over silica (column: 35 g; particle size: 20-40 μm, spherical; eluent: 80% heptane/20% ethyl acetate). After concentrating the fractions under reduced pressure, 165 mg of 5-iodo-2-(1-propylbutyl)isoquinolin-1(2H)-one are obtained in the form of a yellow solid.

$^1$H NMR (300 MHz, DMSO-d6) d ppm 0.83 (t, J=7.1 Hz, 6H) 1.11 (m, 4H) 1.68 (m, 4H) 5.01 (broad m, 1H) 6.65 (d, J=7.8 Hz, 1H) 7.25 (t, J=7.8 Hz, 1H) 7.57 (d, J=7.8 Hz, 1H) 8.24 (d, J=7.8 Hz, 1H) 8.27 (d, J=7.8 Hz, 1H)

MS-EI: 369$^{(+)}$=M$^{(+)}$ 1.1.2: 1-Oxo-2-(1-propylbutyl)-1,2-dihydroisoquinoline-5-carboxylic acid Introduced successively, at a temperature close to 20° C., into a three-necked flask that is stirred and purged using carbon monoxide are 210 mg of 5-iodo-2-(1-propylbutyl)-2H-isoquinoline-1-one, 6 cm$^3$ of dimethylformamide, 0.37 cm$^3$ of water, 0.212 g of potassium acetate, 94 mg of potassium iodide, 25 mg of palladium acetate and 60 mg of triphenylphosphine. The reaction mixture is subjected to a carbon monoxide bubbling, then is heated at 100° C. for 1 h. The reaction mixture is cooled to 20° C. and stirred for 20 h. The dimethylformamide is evaporated using a rotary evaporator under reduced pressure (5 kPa). The residue obtained is taken up in 10 cm$^3$ of water and 10 cm$^3$ of ethyl acetate. The pH is alkalinized with 1 cm$^3$ of 5M sodium hydroxide. The aqueous phase is washed with 10 cm$^3$ of ethyl acetate. It is then acidified while stirring with 1 cm$^3$ of 5M hydrochloric acid (pH=1), then extracted with 10 cm$^3$ of dichloromethane. The organic phase is dried over magnesium sulfate and concentrated using a rotary evaporator under reduced pressure (5 kPa). 0.149 g of 1-oxo-2-(1-propylbutyl)-1,2-dihydroisoquinoline-5-carboxylic acid is obtained in the form of a beige solid.

LC-MS-DAD-ELSD: 286($^-$)=(m-H)($^-$); 288($^+$)=(M+H)($^+$)

$^1$H NMR (300 MHz, DMSO-d6) d ppm 0.84 (t, J=7.3 Hz, 6H) 1.01-1.22 (m, 4H) 1.57-1.82 (m, 4H) 5.03 (broad m, 1H) 7.44-7.61 (m, 3H) 8.27 (dd, J=7.5, 1.5 Hz, 1H) (dd, J=7.5, 1.5 Hz, 1H) 13.04 (broad unresolved m, 1H).

1.1.3: N-[(1S,2R)-1-benzyl-2-hydroxy-3-{[3-(trifluoromethyl)benzyl]amino}-propyl]-1-oxo-2-(1-propylbutyl)-1,2-dihydroisoquinoline-5-carboxamide 77 mg of 1-oxo-2-(1-propylbutyl)-1,2-dihydroisoquinoline-5-carboxylic acid are dissolved in 4.5 cm$^3$ of dichloromethane under an inert atmosphere at a temperature close to 20° C. 110 mg of (2R,3S)-3-amino-4-phenyl-1-{[3-(trifluoromethyl)benzyl]amino}butan-2-ol hydrochloride (1:1), 5 mg of hydroxybenzotriazole, 61 mg of 1-(3-dimethylaminopropyl)-3-ethylcarbodiimide hydrochloride are added to the solution. 0.22 cm$^3$ of N,N-diisopropylethylamine is poured into the reaction medium. The latter is kept stirring for 20 h at ambient temperature. 10 cm$^3$ of water are added to the reaction medium. The organic phase is washed with 5 cm$^3$ of a saturated aqueous solution of sodium chloride, dried over magnesium sulfate and concentrated using a rotary evaporator under reduced pressure (5 kPa). The crude product obtained is purified by flash chromatography over silica (column: 15 g; particle size: 20-40 μm, spherical; flow rate: 20 cm$^3$/min; eluent: 100% ethyl acetate). After concentrating the fractions under reduced pressure, 84 mg of N-[(1S,2R)-1-benzyl-2-hydroxy-3-{[3-(trifluoromethyl)benzyl]amino}propyl]-1-oxo-2-(1-propylbutyl)-1,2-dihydroisoquinoline-5-carboxamide are obtained in the form of a white solid.

LC-MS-DAD-ELSD: 606($^-$)(M−H)($^-$); 608($^+$)=(M+H)($^+$)

$^1$H NMR (400 MHz, DMSO-d6) d ppm 0.82 (t, J=7.4 Hz, 3H) 0.83 (t, J=7.4 Hz, 3H) 0.97-1.16 (m, 4H) 1.53-1.78 (m, 4H) 2.56-2.77 (m, 3H) 3.16 (dd, J=14.0, 3.7 Hz, 1H) 3.63 (m, 1H) 3.83 (d, J=14.2 Hz, 1H) 3.88 (d, J=14.2 Hz, 1H) 4.21 (m, 1H) 5.00 (broad m, 1H) 5.02 (d, J=5.7 Hz, 1H) 6.29 (d, J=8.1 Hz, 1H) 7.14-7.34 (m, 7H) 7.41 (t, J=7.7 Hz, 1H) 7.53 (t, J=7.7 Hz, 1H) 7.58 (broad d, J=7.7 Hz, 1H) 7.65 (broad d, J=7.7 Hz, 1H) 7.71 (broad s, 1H) 8.25 (broad d, J=7.7 Hz, 1H) 8.32 (d, J=9.0 Hz, 1H).

1.2: Salt N-[(1S,2R)-1-benzyl-2-hydroxy-3-{[3-(trifluoromethyl)benzyl]-amino}propyl]-1-oxo-2-(1-propylbutyl)-1,2-dihydroisoquinoline-5-carboxamide hydrochloride (1:1)

84 mg of N-[(1S,2R)-1-benzyl-2-hydroxy-3-{[3-(trifluoromethyl)benzyl]-amino}propyl]-1-oxo-2-(1-propylbutyl)-1,2-dihydroisoquinoline-5-carboxamide are dissolved in 4 cm$^3$ of ethyl ether at a temperature close to 20° C. 0.2 cm$^3$ of a 4M solution of hydrochloric acid in dioxane is added while stirring and under argon. The reaction mixture precipitates. The stirring is stopped. The supernatant is removed and 5 cm$^3$ of ethyl ether are added. This operation is carried out three times. The last suspension is concentrated under reduced pressure (5 kPa). 87 mg of N-[(1S,2R)-1-benzyl-2-hydroxy-3-{[3-(trifluoromethyl)benzyl]amino}propyl]-1-oxo-2-(1-propylbutyl)-1,2-dihydroisoquinoline-5-carboxamide hydrochloride (1:1) are obtained in the form of a white solid.

$^1$H NMR (400 MHz, DMSO-d6) d ppm 0.83 (t, J=7.3 Hz, 3H) 0.84 (t, J=7.3 Hz, 3H) 0.98-1.19 (m, 4H) 1.68 (m, 4H) 2.68 (dd, J=14.1, 11.1 Hz, 1H) 2.96 (m, 1H) 3.12-3.26 (m, 2H) 3.91 (m, 1H) 4.23 (m, 1H) 4.35 (m, 2H) 5.01 (broad m, 1H) 5.96 (d, J=6.6 Hz, 1H) 6.23 (d, J=7.8 Hz, 1H) 7.15-7.33 (m, 6H) 7.41 (dd, J=7.6, 1.8 Hz, 1H) 7.46 (t, J=7.6 Hz, 1H) 7.68 (t, J=7.8 Hz, 1H) 7.79 (broad d, J=7.8 Hz, 1H) 7.88 (broad d, J=7.8 Hz, 1H) 8.01 (broad s, 1H) 8.28 (ddd, J=7.8, 1.8 Hz, 1H) 8.44 (d, J=9.2 Hz, 1H) 9.07 (broad unresolved m, 1H) 9.32 (broad unresolved m, 1H)

LC-MS-DAD-ELSD: 606(−)(M−H)(−); 608(+)=(M+H)(+).

EXAMPLE 2

2.1: Base N-[(1S,2R)-1-benzyl-2-hydroxy-3-{[3-(trifluoromethyl)benzyl]-amino}propyl]-6-chloro-4-oxo-3-(1-propylbutyl)-3,4-dihydroquinazoline-8-carboxamide 2.1.1: 2-amino-5-chloro-3-iodo-N-(1-propylbutyl)benzamide Added successively to a solution of 3 g of methyl 2-amino-5-chloro-3-iodobenzoate in 100 cm³ of toluene, under an inert atmosphere and at a temperature close to 20° C., are 2.2 g of 4-aminoheptane then 12 cm³ of a 2M solution of trimethylaluminum in toluene. The reaction mixture is heated, while stirring, for 16 h at 100° C., then it is cooled to 20° C. in order to then be poured over a mixture of 250 g of water/ice and 150 cm³ of ethyl acetate. The suspension obtained is filtered over a Celite 545 pellet. The aqueous phase is extracted with 3 lots of 100 cm³ of ethyl acetate. The organic phases are combined then washed with 100 cm³ of a saturated aqueous solution of sodium chloride, dried over magnesium sulfate and concentrated using a rotary evaporator under reduced pressure (5 kPa). The 12 g of crude product obtained are purified by flash chromatography over silica (column: 200 g; particle size: 15-40 µm; eluent: 100% dichloromethane). After concentrating the fractions under reduced pressure, 3.21 g of 2-amino-5-chloro-3-iodo-N-(1-propylbutyl)benzamide are obtained.

LC-MS-DAD-ELSD: 393(−)(M−H)(−); 395(+)=(M+H)(+)

¹H NMR (400 MHz, DMSO-d6) d ppm 0.87 (t, J=7.3 Hz, 6H) 1.15-1.52 (m, 8H) 3.93 (m, 1H) 6.37 (broad s, 2H) 7.55 (d, J=2.4 Hz, 1H) 7.76 (d, J=2.4 Hz, 1H) 8.14 (d, J=9.0 Hz, 1H).

2.1.2: 6-Chloro-8-iodo-3-(1-propylbutyl)quinazolin-4(3H)-one

Poured into a solution of 4.43 g of sodium ethylate in 250 cm³ of ethanol is a solution of 3.21 g of 2-amino-5-chloro-3-iodo-N-(1-propylbutyl)benzamide in 120 cm³ of ethanol then 3.3 cm³ of ethyl formate. The reaction mixture is heated under argon at reflux for 16 h. It is then cooled in order to be evaporated using a rotary evaporator under reduced pressure (5 kPa). 200 cm³ of dichloromethane and 150 cm³ of water are added, while stirring, to the concentration residue. The aqueous phase is extracted with 50 cm³ of dichloromethane. The organic phases are combined, washed with 50 cm³ of a saturated aqueous solution of sodium chloride, dried over sodium sulfate and concentrated using a rotary evaporator under reduced pressure (5 kPa). The ochre product obtained is purified by flash chromatography over silica (column: 200 g; particle size: 15-40 µm; eluent: 100% dichloromethane). After concentrating the fractions under reduced pressure, 2.09 g of 6-chloro-8-iodo-3-(1-propylbutyl)quinazolin-4(3H)-one are obtained.

MS-EI: 404(+)=M (+)

¹H NMR (300 MHz, DMSO-d6) d ppm 0.85 (t, J=7.2 Hz, 6H) 1.03-1.29 (m, 4H) 1.62-1.97 (m, 4H) 4.73-4.82 (broad m, 1H) 8.12 (d, J=2.3 Hz, 1H) 8.42 (d, J=2.3 Hz, 1H) 8.57 (s, 1H).

2.1.3: 6-Chloro-4-oxo-3-(1-propylbutyl)-3,4-dihydroquinazoline-8-carboxylic acid Introduced successively, at a temperature close to 20° C., into a three-necked flask that is stirred and purged using carbon monoxide are 2.05 g of 6-chloro-8-iodo-3-(1-propylbutyl)quinazolin-4(3H)-one, 60 cm³ of dimethylformamide, 3 cm³ of water, 1.89 g of potassium acetate, 168 mg of potassium iodide, 455 mg of palladium acetate and 1.063 g of triphenylphosphine. The reaction mixture is subjected to a carbon monoxide bubbling, then is heated at 100° C. for 6 h 30 min. It is cooled to a temperature close to 20° C. in order to be filtered through a Celite 545 pellet, rinsed with 20 cm³ of dimethylformamide and 20 cm³ of ethyl acetate. The filtrate is evaporated using a rotary evaporator under reduced pressure (5 kPa). The orange-colored solution obtained is taken up in a mixture of 100 g of ice/water and 100 cm³ of ethyl acetate. The pH is brought to 10 with 5M sodium hydroxide. After decanting, the aqueous phase is washed with two lots of 40 cm³ of ethyl acetate. The aqueous phase is acidified, while stirring, with a 5M hydrochloric acid solution (pH=1) then extracted with 3 lots of 40 cm³ of ethyl acetate. The organic phases are combined, then washed with 30 cm³ of a saturated aqueous solution of sodium chloride, dried over magnesium sulfate and concentrated using a rotary evaporator under reduced pressure (5 kPa). The yellow/green oil obtained is purified by flash chromatography over silica (column: 90 g; particle size: 15-40 µm; eluent: 100% dichloromethane to 95% dichloromethane/5% methanol gradient). After concentrating the fractions under reduced pressure, 0.28 g of 6-chloro-4-oxo-3-(1-propylbutyl)-3,4-dihydroquinazoline-8-carboxylic acid is obtained.

LC-MS-DAD-ELSD: 321(−³⁵Cl)=(M−H)(−); 323(+)³⁵Cl=(M+H)(+)

¹H NMR (300 MHz, DMSO-d6) d ppm 0.85 (t, J=7.3 Hz, 6H) 1.09-1.28 (m, 4H) 1.67-1.93 (m, 4H) 4.81 (broad m, 1H) 8.23 (d, J=2.5 Hz, 1H) 8.29 (d, J=2.5 Hz, 1H) 8.27 (s, 1H) 14.50 (broad unresolved m, 1H).

2.1.4: N-[(1S,2R)-1-benzyl-2-hydroxy-3-{[3-(trifluoromethyl)benzyl]-amino}propyl]-6-chloro-4-oxo-3-(1-propylbutyl)-3,4-dihydroquinazoline-8-carboxamide Poured into a suspension of 270 mg of 6-chloro-4-oxo-3-(1-propylbutyl)-3,4-dihydroquinazoline-8-carboxylic acid, 344 mg of (2R,3S)-3-amino-4-phenyl-1-{[3-(trifluoromethyl)benzyl]amino}butan-2-ol hydrochloride (1:1), 17 mg of hydroxybenzotriazole and 200 mg of 1-(3-dimethylaminopropyl)-3-ethylcarbodiimide hydrochloride in 27 cm³ of dichloromethane is 0.573 cm³ of N,N-diisopropylethylamine at a temperature close to 20° C. The solution is kept stirring for 20 h at 20° C. 15 cm³ of water are added to the reaction medium. The aqueous phase is extracted with 15 cm³ of dichloromethane. The organic phases are combined, washed with 10 cm³ of a saturated aqueous solution of sodium chloride, dried over sodium sulfate and concentrated using a rotary evaporator under reduced pressure (5 kPa). The 740 mg of product obtained are purified by flash chromatography over silica (column: 70 g; particle size: 15-40 µm; eluent: 100% dichloromethane to 95% dichloromethane/5% methanol gradient). After concentrating the fractions under reduced pressure, 300 mg of N-[(1S,2R)-1-benzyl-2-hydroxy-3-{[3-(trifluoromethyl)benzyl]amino}propyl]-6-chloro-4-oxo-3-(1-propylbutyl)-3,4-dihydroquinazoline-8-carboxamide are obtained.

LC/MS ELSD Tr (min)=4.07; MH+=643+; MH−=641−; MH−+HCO2H=687−;

¹H NMR (400 MHz, DMSO-d6) d ppm 0.85 (t, J=7.5 Hz, 3H) 0.86 (t, J=7.5 Hz, 3H) 1.07-1.25 (m, 4H) 1.70-1.96 (m, 4H) 2.59-2.74 (m, 2H) 2.79 (dd, J=13.8, 9.6 Hz, 1H) 3.04 (dd, J=13.8, 3.9 Hz, 1H) 3.72 (m, 1H) 3.82 (s, 2H) 4.32 (m, 1H) 4.79 (broad m, 1H) 5.06 (broad d, J=5.1 Hz, 1H) 7.12 (t, J=7.5 Hz, 1H) 7.19 (t, J=7.5 Hz, 2H) 7.27 (d, J=7.5 Hz, 2H) 7.45-7.65 (m, 3H) 7.68 (broad s, 1H) 8.14 (d, J=2.6 Hz, 1H) 8.22 (d, J=2.6 Hz, 1H) 8.54 (s, 1H) 10.05 (d, J=9.0 Hz, 1H).

2.2: Salt N-[(1S,2R)-1-benzyl-2-hydroxy-3-{[3-(trifluoromethyl)benzyl]-amino}propyl]-6-chloro-4-oxo-3-(1-propylbutyl)-3,4-dihydroquinazoline-8-carboxamide hydrochloride (1:1)

100 mg of N-[(1S,2R)-1-benzyl-2-hydroxy-3-{[3-(trifluoromethyl)benzyl]-amino}propyl]-6-chloro-4-oxo-3-(1-propylbutyl)-3,4-dihydroquinazoline-8-carboxamide are dissolved in 1.2 cm³ of ethyl ether at a temperature close to 20° C. 0.3 cm³ of a 4M solution of hydrochloric acid in dioxane is added, while stirring and under argon, at a temperature of 5° C. The reaction mixture precipitates, then the precipitate is dissolved. 5 cm³ of ethyl ether are added. The solution is concentrated under reduced pressure (5 kPa). 95 mg of N-[(1S,2R)-1-benzyl-2-hydroxy-3-{[3-(trifluoromethyl)benzyl]amino}propyl]-6-chloro-4-oxo-3-(1-propylbutyl)-3,4-dihydroquinazoline-8-carboxamide hydrochloride (1:1) are obtained in the form of an amorphous beige.

LC/MS ELSD Tr (min)=4.04; MH+=643+; MH−=641−; MH−+HCO2H=687

NMR: 0.87 (t, J=7.5 Hz, 3H); 0.88 (t, J=7.5 Hz, 3H); from 1.12 to 1.25 (m, 4H); 1.80 (m, 2H); 1.89 (m, 2H); 2.80 (dd, J=10.5 and 14.0 Hz, 1H); 2.97 (m, 1H); 3.17 (dd, J=3.0 and 14.0 Hz, 1H); 3.22 (m, 1H); 3.96 (m, 1H); from 4.17 to 4.31 (m, 3H); 4.81 (broad m, 1H); 5.89 (broad unresolved m, 1H); 7.15 (t, J=7.5 Hz, 1H); 7.22 (t, J=7.5 Hz, 2H); 7.32 (d, J=7.5 Hz, 2H); 7.64 (t, J=7.5 Hz, 1H); 7.73 (d, J=7.5 Hz, 1H); 7.81 (d, J=7.5 Hz, 1H); 7.92 (s, 1H); 8.10 (d, J=2.5 Hz, 1H); 8.24 (d, J=2.5 Hz, 1H); 8.58 (s, 1H); 9.10 (broad unresolved m, 2H); 10.0 (d, J=8.5 Hz, 1H).

EXAMPLE 3

3.1: Base N-[(1S,2R)-1-benzyl-2-hydroxy-3-{[3-(trifluoromethyl)benzyl]-amino}propyl]-4-oxo-3-(1-propylbutyl)-3,4-dihydroquinazoline-8-carboxamide 195 mg of N-[(1S,2R)-1-benzyl-2-hydroxy-3-{[3-(trifluoromethyl)benzyl]-amino}propyl]-6-chloro-4-oxo-3-(1-propylbutyl)-3,4-dihydroquinazoline-8-carboxamide, 5 cm³ of dioxane and 30 mg of 10% (50% wet with water) palladium on carbon are stirred under 10 bar of hydrogen in an autoclave. Since the reaction does not develop, 30 mg of 10% dry palladium on carbon are added and the reaction mixture is stirred under 15 bar of hydrogen in an autoclave. The catalyst is filtered and the filtrate is concentrated under reduced pressure (5 kPa). 185 mg of N-[(1S,2R)-1-benzyl-2-hydroxy-3-{[3-(trifluoromethyl)benzyl]amino}propyl]-4-oxo-3-(1-propylbutyl)-3,4-dihydroquinazoline-8-carboxamide are obtained.

LC-MS-DAD-ELSD: 653$^{(+)}$=(M+formic acid-H)$^{(+)}$; 609$^{(+)}$=(M+H)$^{(+)}$ ¹H NMR (400 MHz, DMSO-d6) d ppm 0.87 (t, J=7.3 Hz, 3H) 0.88 (t, J=7.3 Hz, 3H) 1.11-1.30 (m, 4H) 1.72-2.01 (m, 4H) 2.81 (dd, J=14.1, 9.8 Hz, 1H) 2.98 (d, J=12.5, 9.8 Hz, 1H) 3.19 (dd, J=14.1, 4.2 Hz, 1H) 3.28 (partially masked m, 1H) 3.99 (m, 1H) 4.17-4.32 (m, 3H) 4.86 (broad m, 1H) 5.93 (broad s, 1H) 7.14 (t, J=7.5 Hz, 1H) 7.21 (t, J=7.5 Hz, 2H) 7.33 (d, J=7.5 Hz, 2H) 7.58-7.67 (m, 2H) 7.73 (broad d, J=7.8 Hz, 1H) 7.83 (d, J=7.8 Hz, 1H) 7.95 (broad s, 1H) 8.24 (dd, J=8.0, 1.6 Hz, 1H) 8.30 (dd, J=8.0, 1.6 Hz, 1H) 8.59 (s, 1H) 9.20 (broad unresolved m, 1H) 10.14 (d, J=8.3 Hz, 1H).

3.2: Salt N-[(1S,2R)-1-benzyl-2-hydroxy-3-{[3-(trifluoromethyl)benzyl]-amino}propyl]-4-oxo-3-(1-propylbutyl)-3,4-dihydroquinazoline-8-carboxamide hydrochloride (1:1)

180 mg of N-[(1S,2R)-1-benzyl-2-hydroxy-3-{[3-(trifluoromethyl)benzyl]-amino}propyl]-4-oxo-3-(1-propylbutyl)-3,4-dihydroquinazoline-8-carboxamide are dissolved in 2.5 cm³ of ethyl ether at a temperature close to 20° C. 0.53 cm³ of a 4M solution of hydrochloric acid in dioxane is added, while stirring and under argon, at a temperature of 5° C. The reaction mixture precipitates. The suspension is stirred for 10 min then the stirring is stopped in order to remove the supernatant. 5 cm³ of ethyl ether are again added. This operation is carried out 3 times. The last suspension is then concentrated under reduced pressure (5 kPa). 160 mg of N-[(1S,2R)-1-benzyl-2-hydroxy-3-{[3-(trifluoromethyl)benzyl]amino}propyl]-4-oxo-3-(1-propylbutyl)-3,4-dihydroquinazoline-8-carboxamide hydrochloride (1:1) are obtained in the form of a pale yellow solid.

NMR: 0.87 (t, J=7.5 Hz, 3H); 0.88 (t, J=7.5 Hz, 3H); 1.19 (m, 4H); 1.80 (m, 2H); 1.91 (m, 2H); 2.81 (dd, J=10.5 and 14.0 Hz, 1H); 3.01 (m, 1H); 3.19 (dd, J=3.0 and 14.0 Hz, 1H); 3.27 (m, 1H); 3.99 (partially masked m, 1H); 4.21 (m, 1H); 4.31 (m, 2H); 4.84 (broad m, 1H); 5.96 (very broad unresolved m, 1H); 7.14 (t, J=7.5 Hz, 1H); 7.22 (t, J=7.5 Hz, 2H); 7.33 (d, J=7.5 Hz, 2H); 7.61 (t, J=8.0 Hz, 1H); 7.64 (t, J=7.5 Hz, 1H); 7.75 (d, J=7.5 Hz, 1H); 7.84 (d, J=7.5 Hz, 1H); 7.95 (s, 1H); 8.24 (dd, J=1.5 and 8.0 Hz, 1H); 8.30 (dd, J=1.5 and 8.0 Hz, 1H); 8.58 (s, 1H); 9.04 (broad unresolved m, 1H); 9.22 (broad unresolved m, 1H); 10.15 (d, J=8.5 Hz, 1H).

LC-MS-DAD-ELSD: 653$^{(-)}$=(M+formic acid-H)$^{(-)}$; 609$^{(+)}$=(M+H)$^{(+)}$

MP: 152° C.

Table 1 below illustrates the chemical structures and the physical properties of some examples of compounds according to the invention. In this table:

MP (° C.) represents the melting point of the compound in degrees Celsius;

in the "salt" column, "-" represents a compound in the free base form, whereas "HCl" represents a compound in the hydrochloride form and the ratio between parentheses is the (acid:base) ratio;

"nd" signifies not determined;

Me represents a methyl group; and

R3 represents a trifluoromethyl group.

The compounds described in this table were prepared according to the methods described previously.

TABLE 1

[Chemical structure showing a quinazolinone-based compound with substituents R1, R2, R3, R4, R5, R6, X, and an amide linkage with OH group]

| Compound | R₁ | X | R₂ | R₄, R₅ | R₆ | Salt | MP (° C.) |
|---|---|---|---|---|---|---|---|
| 1 | (n-C₃H₇)₂CH— | C | H | H—, H— | H— | HCl (1:1) | nd[a] |
| 2 | (n-C₃H₇)₂CH— | N | H— | H—, H— | 6-Cl— | HCl (1:1) | nd[b] |
| 3 | (n-C₃H₇)₂CH— | N | H— | H—, H— | H— | HCl (1:1) | 152 |

[a] characterized by a ¹H NMR spectrum and by liquid chromatography coupled to a mass spectrometer
[b] characterized by a ¹H NMR spectrum The compounds according to the invention have been the subject of pharmacological tests enabling their inhibitory effect with respect to β-secretase activity to be determined.

The tests consisted in measuring the in vitro inhibition of the β-secretase activity by the compounds of the invention, via the use of the "BACE-1 FRET Assay Kit, Red" available from PanVera-Invitrogen Inc.

The β-secretase activity measured corresponds to that of a purified recombinant form of human BACE1 aspartyl protease (the latter comprising a hexahistidine tag at the C-terminal position) produced by expression in Drosophila cells. The purified enzyme is conditioned in TRIS buffer (18 mM) at pH 7.5 containing NaCl (0.45M), $MnCl_2$ (0.9 mM), $CaCl_2$ (0.9 mM), α-D-methylmannoside and 10% glycerol, and stored at −80° C. until use.

The BACE1 activity is measured from the cleavage of a fluorogenic peptide substrate sold by Invitrogen (PanVera BACE1/β-secretase FRET assay kit, Red; reference P2985), based on the principle of fluorescence resonance energy transfer (FRET) and corresponding to the Rh-EVNLDAEFK-Quencher sequence; the cleavage of the peptide is measured from the increase of the fluorescent signal emitted by the rhodamine derivative (Rh).

The test is carried out in a 96-well microplate in order to determine the inhibition of the enzyme activity by the products of the invention. The commercial solution of peptide substrate (PanVera, reference P2986) is at a concentration of 75 μM in 50 mM ammonium bicarbonate, and stored at −20° C. in the dark until use. The dilutions of the products to be tested are prepared in DMSO starting from a 10 mM stock solution. The products of the invention, at final concentrations of 0.003 to 100 μM are incubated at ambient temperature with the peptide substrate (final concentration of 0.25 μM) and the purified enzyme (final concentration of 10 nM) in sodium acetate buffer (50 mM, pH 4.5) (buffer from the commercial kit, reference P2988), generally for 60 min, in the dark. The final percentage of DMSO does not exceed 10%. When the incubation is finished, the fluorescence is measured in a spectrofluorimeter, at the excitation wavelength of about 543 nm and emission wavelength of about 585 nm. For each product concentration tested, the fluorescent signal is compared to the maximum signal obtained when the peptide substrate is only incubated with the enzyme.

The inhibitory activity of the products of the invention is then evaluated by the measurement of the $IC_{50}$ (concentration of product giving 50% inhibition of the enzyme activity) using a non-linear regression analysis (computer application software XLfit, IDBS™).

The $IC_{50}$ values are between 0.1 μM and 5 μM.

For example, compounds No. 1 and 3 showed an $IC_{50}$ of 2.6 μM and 0.83 μM respectively.

It therefore appears that the compounds according to the invention have an inhibitory activity with respect to the activity of β-secretase.

The compounds according to the invention may therefore be used for the preparation of medicaments, in particular medicaments that inhibit the production of Aβ.

Thus, another subject of the invention is, according to another of its aspects, medicaments which comprise a compound of formula (I) or an addition salt of the latter with a pharmaceutically acceptable acid.

These medicaments find their use in therapeutics, especially in the treatment and prevention of diseases associated with the production of the Aβ peptide, among which mention may be made of neurodegenerative diseases such as Alzheimer's disease, Parkinson's disease, Huntington's disease, Creutzfeldt-Jakob disease, Down's syndrome, dementia with Lewy bodies, senile dementia, frontotemporal dementia, cerebral and systemic amyloidosis, mild cognitive impairments, cerebral amyloid angiopathy, primary and secondary memory disorders, amyotrophic lateral sclerosis, multiple sclerosis, peripheral neuropathies, diabetic neuropathies, migraine, mood disorders, depression, anxiety, vascular disorders such as atherosclerosis, cerebrovascular ischemia, tumors and cell proliferation disorders.

These medicaments find, in particular, their use in the treatment and the prevention of neurodegenerative diseases such as Alzheimer's disease, Parkinson's disease, Down's syndrome, dementia with Lewy bodies, senile dementia, frontotemporal dementia, cerebral and systemic amyloidosis, mild cognitive impairments, cerebral amyloid angiopathy, primary and secondary memory disorders and cerebrovascular ischemia.

According to another of its aspects, the present invention relates to pharmaceutical compositions comprising, as active principle, a compound according to the invention. These pharmaceutical compositions contain an effective dose of at least one compound according to the invention, or a pharmaceutically acceptable salt, and also at least one pharmaceutically acceptable excipient.

Said excipients are chosen, depending on the pharmaceutical form and the desired method of administration, from the customary excipients which are known to a person skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or its optional salt, solvate or hydrate, may be administered in unit administration form, as a mixture with conventional pharmaceutical excipients, to animals and human beings for the prophylaxis or the treatment of the above disorders or diseases.

The suitable unit administration forms comprise oral forms, such as tablets, soft or hard gelatin capsules, powders, granules and oral solutions or suspensions, sublingual, buccal, intratracheal, intraocular and intranasal administration forms, forms for administration by inhalation, topical, transdermal, subcutaneous, intramuscular or intravenous administration forms, rectal administration forms and implants. For topical application it is possible to use the compounds according to the invention in creams, gels, ointments or lotions.

By way of example, a unit administration form of a compound according to the invention in tablet form may comprise the following components:

| | |
|---|---|
| Compound according to the invention | 50.0 mg |
| Mannitol | 223.75 mg |
| Croscarmellose sodium | 6.0 mg |
| Maize starch | 15.0 mg |
| Hydroxypropyl methyl cellulose | 2.25 mg |
| Magnesium stearate | 3.0 mg |

The present invention, according to another of its aspects, also relates to a method for treating the pathologies indicated above which comprises the administration, to a patient, of an effective dose of a compound according to the invention, or one of its pharmaceutically acceptable salts or hydrates or solvates.

We claim:

1. A compound of formula (I):

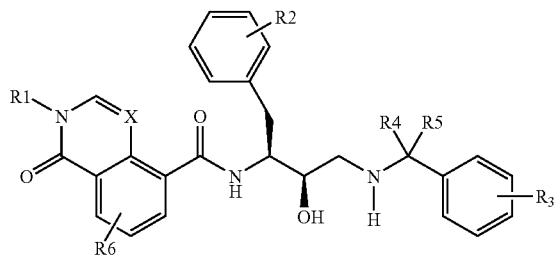

(I)

wherein:

R1 is hydrogen, $(C_1-C_{10})$alkyl, $(C_3-C_7)$cycloalkyl, $(CH_2)_n$—$(C_2-C_6)$alkenyl, $(CH_2)_n$—$(C_2-C_6)$alkynyl, $(C_1-C_6)$alkyl-Z—$(C_1-C_6)$alkyl, COOR, $S(O)_m R$, aryl or aralkyl, wherein the $(C_1-C_{10})$alkyl, $(C_3-C_7)$cycloalkyl, $(CH_2)_n$—$(C_2-C_6)$alkenyl, $(CH_2)_n$—$(C_2-C_6)$alkynyl, $(C_1-C_6)$alkyl-Z—$(C_1-C_6)$alkyl, aryl and aralkyl are optionally substituted with one or more groups chosen from halogen, $(C_1-C_6)$alkyl, $(C_3-C_7)$cycloalkyl, halo$(C_1-C_6)$alkyl, $(C_1-C_6)$alkoxy, halo$(C_1-C_6)$alkoxy, NR7R8, nitro, cyano, OR, COOR, CONR7R8, $S(O)_m$NR7R8 and aryl;

R2 is one or more groups chosen from hydrogen, halogen, $(C_1-C_6)$alkyl, $(C_3-C_7)$cycloalkyl, $(C_2-C_6)$alkenyl, $C_2-C_6$ alkynyl, $(C_1-C_6)$alkyl-Z—$(C_1-C_6)$alkyl, halo$(C_{1-6})$alkyl, halo$(C_1-C_6)$alkoxy, hydroxy, $(C_1-C_6)$alkoxy, nitro, cyano, amino, NR7R8, COOR, CONR7R8, OCO$(C_1-C_6)$alkyl, $S(O)_m$—NR7R8 and aryl, wherein the aryl is optionally substituted with one or more groups chosen from halogen, $(C_1-C_6)$alkyl, $(C_3-C_7)$cycloalkyl, halo$(C_1-C_6)$alkyl, $(C_1-C_6)$alkoxy, halo$(C_1-C_6)$alkoxy, NR7R8, OR, nitro, cyano, COOR, CONR7R8 and $S(O)_m$NR7R8;

R3 is trifluoromethyl;

R4 and R5 are hydrogen, or

R4 and R5 taken together with the carbon atom to which they are attached form a saturated ring containing from 3 to 6 carbon atoms and optionally containing from 0 to 1 heteroatom chosen from O, N and S;

R6 is hydrogen, halogen, $(C_1-C_6)$alkyl, $(C_3-C_7)$cycloalkyl, $(C_3-C_7)$cycloalkyl$(C_1-C_6)$alkyl, halo$(C_1-C_6)$alkyl, nitro, amino, NR7R8, COOR, NR7$(SO_2)$R8, CONR7R8 or aryl, wherein the aryl is optionally substituted with one or more groups chosen from halogen, $(C_1-C_6)$alkyl, $(C_1-C_6)$alkoxy and cyano;

R, R7 and R8 are, independently of one another, hydrogen, $(C_1-C_6)$alkyl, $(C_3-C_7)$cycloalkyl, $(C_3-C_7)$cycloalkyl$(C_1-C_6)$alkyl, aryl or aryl$(C_1-C_6)$alkylene, or R7 and R8 taken together with the nitrogen atom to which they are attached may form a saturated, partially unsaturated or unsaturated ring containing from 5 to 7 carbon atoms and optionally containing, in addition, a heteroatom chosen from O, N and $S(O)_m$;

X is a nitrogen atom;

Z is O, N and $S(O)_m$;

m is 0, 1 or 2; and n is 1, 2, 3, 4, 5 or 6;

or a pharmaceutically acceptable acid addition salt thereof.

2. The compound according to claim 1, wherein

R1 is $(C_1-C_{10})$alkyl, which is optionally substituted with one or more $(C_1-C_6)$alkyl groups;

R2, R4 and R5 are hydrogen; and

R6 is hydrogen or halogen;

or a pharmaceutically acceptable acid addition salt thereof.

3. The compound according to claim 1, which is selected from:

N-[(1S,2R)-1-benzyl-2-hydroxy-3-{[3-(trifluoromethyl)benzyl]amino}propyl]-6-chloro-4-oxo-3-(1-propylbutyl)-3,4-dihydroquinazoline-8-carboxamide and its hydrochloride; and N-[(1S,2R)-1-benzyl-2-hydroxy-3-{[3-(trifluoromethyl)benzyl]amino}propyl]-4-oxo-3-(1-propylbutyl)-3,4-dihydroquinazoline-8-carboxamide and its hydrochloride.

4. A pharmaceutical composition, comprising the compound according to claim 1, or a pharmaceutically acceptable acid addition salt thereof and at least one pharmaceutically acceptable excipient.

5. A pharmaceutical composition, comprising the compound according to claim 2, or a pharmaceutically acceptable acid addition salt thereof and at least one pharmaceutically acceptable excipient.

6. A pharmaceutical composition comprising the compound according to claim 3 or a pharmaceutically acceptable salt thereof, in combination with at least one pharmaceutically acceptable excipient.

* * * * *